United States Patent [19]

Pratt et al.

[11] Patent Number: 5,080,679
[45] Date of Patent: Jan. 14, 1992

[54] ORTHOPEDIC JUNCTION FOR DISSIMILAR MATERIALS

[75] Inventors: Clyde R. Pratt, Somis; Roger G. Carignan, Thousand Oaks, both of Calif.

[73] Assignee: Techmedica, Inc., Camarillo, Calif.

[21] Appl. No.: 471,411

[22] Filed: Jan. 29, 1990

[51] Int. Cl.$^5$ .............................................. A61F 2/34
[52] U.S. Cl. .......................................... 623/23; 623/18
[58] Field of Search ...................... 623/16, 18, 20, 22, 623/23

[56] References Cited

U.S. PATENT DOCUMENTS

| | | | |
|---|---|---|---|
| 4,227,265 | 10/1980 | Frey | 623/23 |
| 4,670,015 | 6/1987 | Freeman | 623/23 |
| 4,921,500 | 5/1990 | Averill et al. | 623/18 |

FOREIGN PATENT DOCUMENTS

| | | | |
|---|---|---|---|
| 3802213 | 7/1989 | Fed. Rep. of Germany | 623/18 |
| 2310120 | 12/1979 | France | 623/23 |
| 2493139 | 5/1982 | France | 623/23 |

*Primary Examiner*—David J. Isabella
*Attorney, Agent, or Firm*—Cislo & Thomas

[57] ABSTRACT

An improved orthopedic junction for releasably connecting prosthetic materials having varying characteristics comprising an apparatus of an inner component of a first material having certain characteristics including a female receptor for receiving a male end of a prosthesis of the first material. The female receptor and the male end are complementarily tapered to provide a locking taper connection therebetween when the male end is inserted into the female receptor. An outer component is incorporated which comprises a second material having different material characteristics from the first material. The outer component partially surrounds the inner component and fixedly and securely retains the inner component, preventing the first component from moving, rotating, or sliding relative to the second component. This provides a secure, but dissociable junction between the outer piece and the end of the prosthesis.

The method of the invention provides attachment of an interchangeable prosthesis using dissimilar materials comprising the steps of selecting an implantable retainer for providing a contact surface which will not induce tissue growth or which has superior wear properties. The retainer includes a sleeve of a selected material. Next, a prosthesis of a selected material is selected having an end to mate and to securably engage the sleeve. The sleeve and the prosthesis are fixedly securable and are separable in the event an alternatively-sized prosthesis must be implanted. Finally, the prosthesis is implanted with the retainer in a body and mated to the end of the prosthesis with the sleeve to provide a secure engagement between the retainer and the prosthesis.

20 Claims, 2 Drawing Sheets

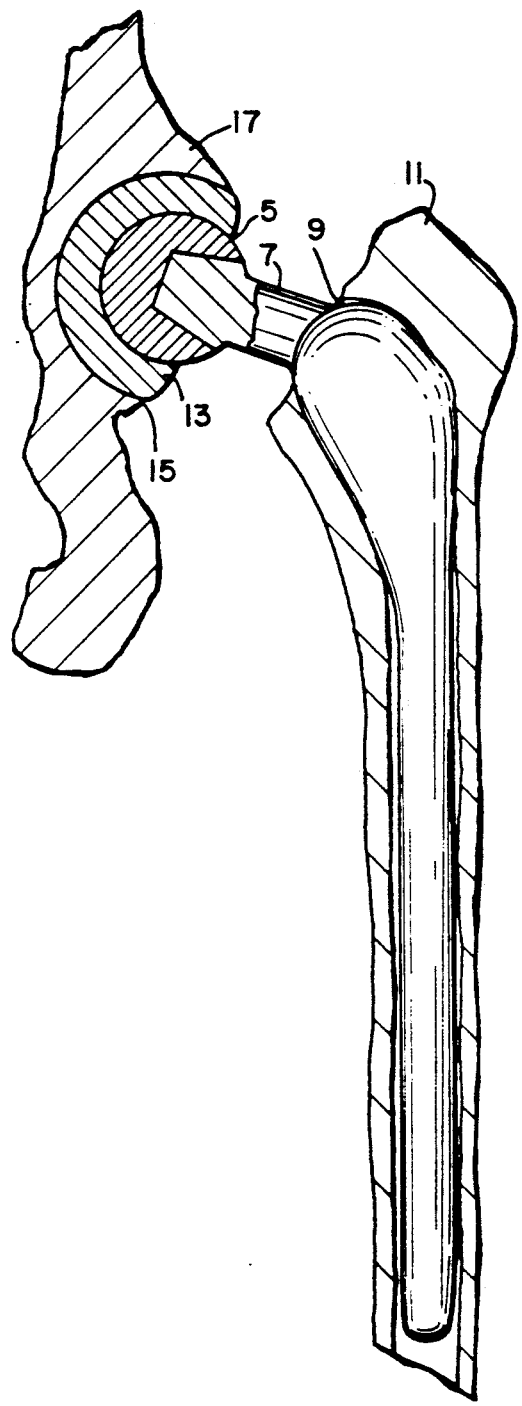
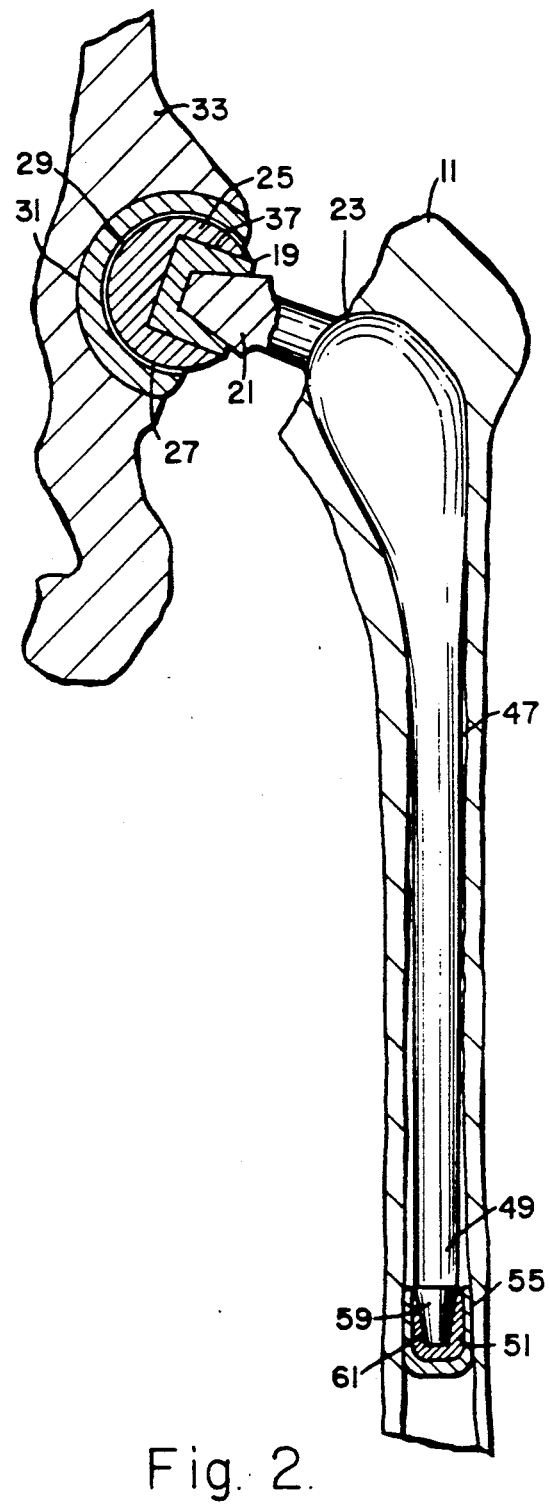
Fig. 1.
(PRIOR ART)
Fig. 2.

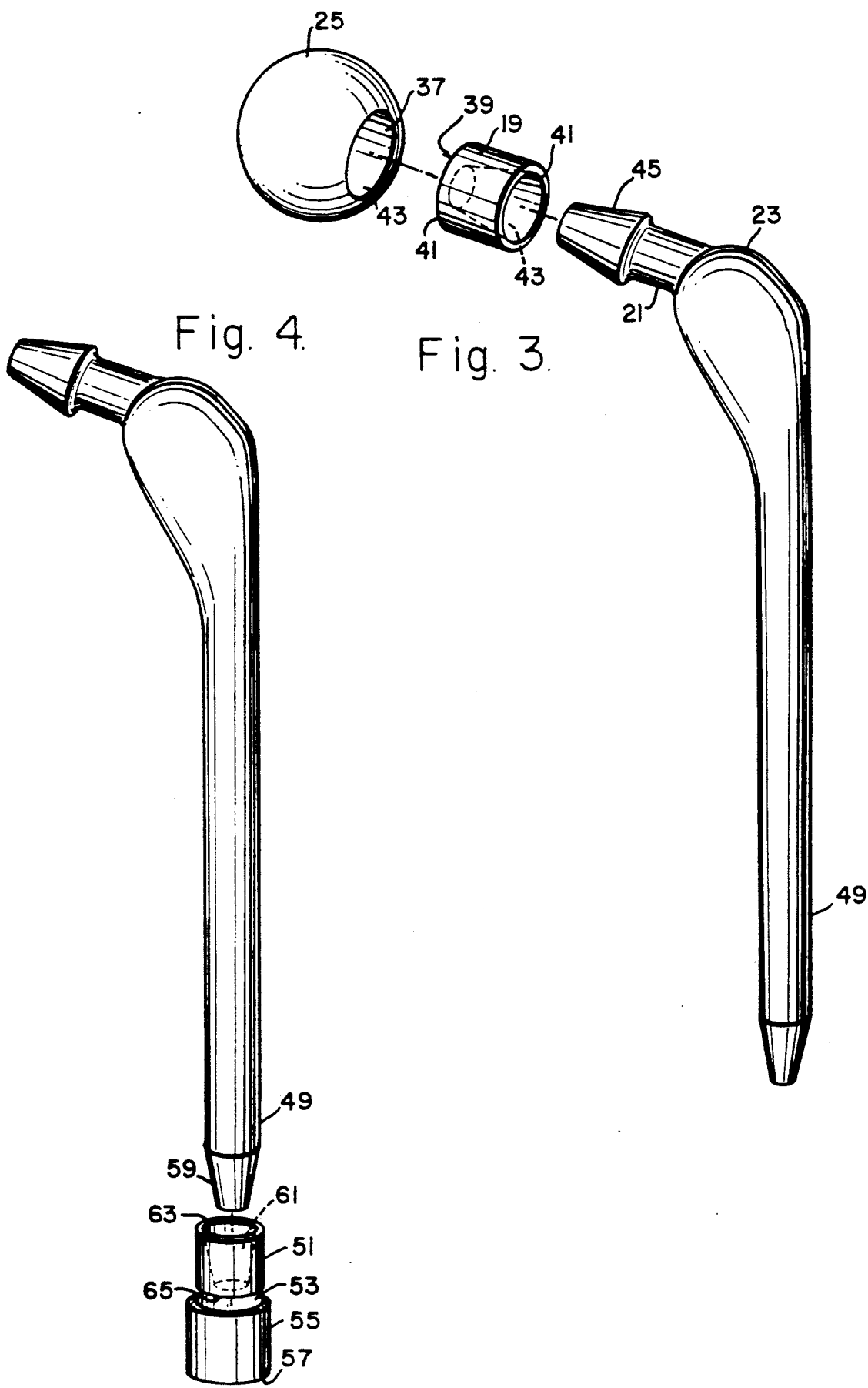

ORTHOPEDIC JUNCTION FOR DISSIMILAR MATERIALS

BACKGROUND OF THE INVENTION

This invention relates to an improved orthopedic connector for joining a portion of a prosthesis of a selected material with a second portion of the prosthesis of a dissimilar material.

Many endoprostheses have been developed to replace many of the bones of the body which must be replaced due to disease or trauma. These prostheses must have a number of characteristics ranging from strength, durability, hardness, resilience, ability to receive tissue attachment at some locations, ability to resist tissue attachment at other locations and various other characteristics. Many of these prostheses so designed cannot possibly fill all of the characteristics necessary over the entire length of the prosthesis to achieve the desirable characteristics at various points along the length or breadth of the prosthesis.

It is desirable for a hip joint prostheses as shown in FIG. 1 to have a ball member 5 made of an alumina, cobalt chrome alloy, or some other hard material which enhances the wear characteristics of a femoral ball/cup combination attached to a prosthesis 9 to replicate the articulation of a human joint. A proximal stem 7 of the prosthesis 9 can be made of titanium, titanium alloy, nickel-chrome alloy, 316 LVM stainless steel or cobalt-chrome-molybdenum alloy. The ball member 5 can be captively or loosely held within a socket 13 which is made of an ultra high molecular weight, high-density polyethylene, alumina or other accepted biocompatible material which is fixed in the pelvis 17. A distal stem 16 can inserted into an intramedullary canal 9 of a femur bone 11.

An ideal combination of materials between the distal stem 7 and the ball member 5 has not been easily achievable because of the many disadvantages associated with the coupling of dissimilar materials or materials having different degrees of hardness. Typically, an implanting surgeon cannot necessarily select an optimum implant alloy for specific functions within the structure of a prosthesis without risking the potentially severe problems associated with self locking tapers or couplings between dissimilar metal alloys.

For example, titanium alloy is generally considered to be a very bio-compatible material. Clinical studies have shown that bone and tissue will adhere directly to the alloy without the interposition of an encapsulating fibrous layer. This phenomena has been utilized by prosthesis designers to design femoral components which are fixed to the patient without bone cement. On the other hand, titanium alloy wear characteristics are not optimal. Therefore, existing practice in this area calls for the use of femoral heads made of cobalt-chrome-molybdenum alloy, or ceramic material, which are held on the prosthesis by a self-locking taper junction or the like.

Movement between the two bodies of dissimilar material can create wear debris or metal ion release with is extremely disadvantageous to the surrounding tissue and its subsequently healing, and may affect the longevity of the implanted device.

U.S. Pat. No. 4,636,218 issued to Isamu Fukuura and Shigeo Niwa issued Jan. 13, 1987 shows such a combination of materials between a prosthesis stem and a ball member of dissimilar materials. Great lengths must be taken to use various materials of differing chemical properties which are compatible and reduce the risk of wear debris or metal ion release.

Still, the inherent dissimilarity in hardness of the materials and their differing mechanical properties create potential problems, especially in the implantation and fitting process where the implanting surgeon may choose from a variety of prostheses over the course of the operation to properly fit the prosthesis to the situation encountered. It must be remembered that often times, the surgeon must resect the top of the femur at differing locations depending upon the disease or trauma or other circumstances encountered on exposing the hip joint to be replaced.

Additionally, current surgical techniques call for the use of distal intramedullary canal spacers which are attached to the lower end of the prosthesis stem using self-locking tapers or the like incorporated to allow secure engagement between the distal end of the stem and the spacer. In such cases, the implanting surgeon may want to avoid boney ongrowth into the spacer, because such ongrowth would inadvertently affect bone remodeling and prevent removal of the prosthesis if the prosthesis should require future revision.

Again, dissimilar materials are often preferable wherein a titanium alloy prosthesis stem is much more durable. However, tissue and bone attachment may take place between the prosthesis stem and the intramedullary canal which would make future prosthesis revision more difficult. A distal spacer of a material to inhibit such ongrowth would be desirable but the problems which arise by the generation of unwanted metal wear debris and ion release when such dissimilar materials are so coupled together may prohibit such an arrangement.

There is great commercial interest in the prosthesis industry to manufacture and market improved orthopedic junctions which would eliminate the problems of using dissimilar materials, especially alloys having different degrees of hardness and yet, also allow interchangeability of various prosthesis components. There is a great interest in finding a simple and inexpensive solution to the above-mentioned problems without having to develop exotic materials or processes or exotic combinations thereof in an attempt to achieve proper coupling without jeopardizing the durability, strength, bicompatability and effectiveness of endoprostheses.

The features identified above as being desired for orthopedic junctions for implantable prostheses are all provided by the present invention.

SUMMARY OF THE INVENTION

The present invention is embodied in an improved orthopedic connector for joining a prosthesis of a selected material comprising a sleeve means for mating with a mating end of a prosthesis. The sleeve means is of a compatible material to the selected material of the prosthesis.

A retaining means is incorporated for retaining the sleeve means fixed relative to the retaining means and preventing the sleeve means from dissociating from the retaining means. The retaining means is of a dissimilar material to the selected material and chosen for its specific properties. The dissimilar material may be of the type which prohibits bone and tissue ongrowth and inhibits bone attachment thereto or optimizes wear properties.

The sleeve means can include an inner recess which is inwardly tapered at a connection end for receiving the mating end of the prosthesis which is tapered outwardly. The mating of the sleeve means with the mating end of the prosthesis can form a self-locking taper connection which is securable upon association, but which can be dissociated if future revision of the prosthesis is necessary.

The sleeve means can include a closed end opposite its connection end and the sleeve means can be recessed within the retaining means.

In one embodiment, the selected material of the prosthesis is a titanium alloy chosen for its biocompatability, strength, and durability and the similar material of the prosthesis is a titanium alloy. The dissimilar material of the retaining means is a cobalt-chrome-molybdenum alloy chosen for its hardness, wear properties, and ability to resist tissue ongrowth.

In an alternative embodiment, an improved orthopedic junction releaseably connects prosthetic materials having different degrees of hardness. An inner component of a first material having a first degree of hardness includes a female receptor means for receiving a male end of a prosthesis of the first material. The female receptor means and the male end are complementarily tapered to provide a self-locking taper connection therebetween when the male end is inserted into the female receptor means.

An outer component of the second material has a different degree of hardness from the first material. The outer component partially surrounds the inner component and fixedly and securely retains the inner component therein preventing the first component from moving, rotating or sliding relative to the second component. This provides a secure, but dissociable junction between the outer piece and the male end of the prosthesis.

The outer component can have a convexly curved exterior surface of a shape and size to interface with a hip socket of a pelvis. The prosthesis is of a type which is insertable within an intramedullary canal of a femur, thereby providing a hip joint prosthesis of dissimilar materials optimized for the greatest durability and implantability.

Supplementing the above configuration, a second implantable retaining means provides a contact surface which will not induce tissue growth thereto. A second retaining means includes a second sleeve means of a selected material. The second sleeve means and intramedullary end of the prosthesis are fixedly engageable and separable. An alternatively-sized prosthesis may be implanted by the implanting surgeon. Such a connection can be a self-locking taper or the like between the intramedullary end of the prosthesis and the second sleeve means.

The invention is also a method for providing an attachment of an interchangeable prosthesis using dissimilar metals comprising the steps of selecting an implantable retaining means for providing a contact surface which will not induce tissue growth thereto. The retaining means includes a sleeve means of a selected material. The second step is selecting a prosthesis of the selected material having an end to mate and to secure the sleeve means. The sleeve means and the prosthesis are fixedly securable and separable in the event an alternatively-sized prosthesis must be implanted.

The next step is implanting the prosthesis and the retaining means in a body and mating the end of the prosthesis with the sleeve means to provide secure engagement between the retaining means and the prosthesis. The sleeve means includes an inner surface which is inwardly tapered at a connection end for receiving the end of the prosthesis which is tapered outwardly.

Mating of the sleeve means with the end of the prosthesis forms a self-locking taper connection therebetween. The selected material of the sleeve means and the prosthesis can be of a titanium alloy and the retaining means can be of a cobalt-chrome-molybdenum alloy.

This method can be appropriately incorporated with the implantation of a femoral-type prosthesis having an intramedullary end which is implantable within the intramedullary canal of the femur. The retaining means has a convexly rounded exterior surface to slidably engage a socket including a complementary contact surface. The socket is embedded in the pelvis of the body to simulate a hip joint.

Alternatively, the method can include the further step of selecting a second implantable retaining means for providing a contact surface, which does not induce tissue growth thereto. The second retaining means includes a second sleeve means of a selected material. The second sleeve means and the intramedullary end of the prosthesis are fixedly engageable and separable in the event that an alternatively-sized prosthesis may be implantable. Next, the second retaining means is implantable in the body and mated with the intramedullary end of the prosthesis with the second sleeve means to provide a secure engagement between the second retaining means and the intramedullary end of the prosthesis.

The second retaining means may be inserted within the intramedullary canal of the body and has a conical exterior surface with cylindrical walls which engage interior walls of the intramedullary canal. The second retaining means can act as a spacer between the second sleeve means and the walls of the intramedullary canal, and preclude tissue and bone attachment thereto.

BRIEF DESCRIPTION OF THE DRAWING

FIG. 1 is a longitudinal cross-sectional view of a conventional artificial articulation for a hip joint;

FIG. 2 is a longitudinal cross-sectional view of a first embodiment of an artificial articulation according to the present invention;

FIG. 3 is a perspective view of a hip prosthesis and an exploded view of a femoral end of the prosthesis according to the present invention with recesses as shown in phantom line;

FIG. 4 is a perspective exploded view of a further embodiment of an orthopedic junction according to the present invention with recesses shown in phantom line;

DESCRIPTION OF THE PREFERRED EMBODIMENTS

According to embodiments of the present invention wherein like numerals represent like features throughout as shown in FIGS. 2–4, the invention comprises a sleeve 19 shown in cross-section in FIG. 2 in association with a proximal stem 21 of a femoral prosthesis 23. The sleeve 19 is retained within a specially-fitted ball member 25.

The ball member 25 has a convexly curved exterior surface 27 for association and articulation with a concavely curved interior surface 29 of an ultra high molecular weight polyethylene socket 31 which is fastened to a hip bone or pelvis 33 by way of a bonding cement or tissue ingrowth.

The ball member 25 may be of a very hard material such as cobalt-chrome-molybdenum alloy and being of such a hard surface that wear between the ultra high molecular weight polyethylene socket 31 and the ball member 25 is minimized. Within the ball member 25, a recess 37 is sized to receive the sleeve 19. The sleeve 19 may be shrink-fitted, welded, diffusion bonded or otherwise attached to provide a secure attachment between the ball member 25 and the sleeve 19 to prevent relative movement therebetween, particularly rotation, sliding or any other articulation to prevent scraping between the sleeve 19 and the ball member 25.

As particularly shown in FIG. 3, the sleeve 19 may have a closed end 39, but has an exterior overall surface 41 which is entirely complementary to interior walls 43 of the ball member 25 so a secure fit between the sleeve 19 and the ball member 25 is achieved in addition to the shrink-fitting, welding, or diffusion bonding used. The sleeve 19 may be of a titanium alloy or another material which is dissimilar to the material used for the ball member 25 and has a degree of hardness different therefrom.

The sleeve 19 includes a second recess 41 shown in phantom line in FIG. 3 which ma be axially defined therein having inwardly tapered walls 48 to complement exterior walls 45 of the proximal stem 21 of the prosthesis 23.

In the preferred embodiment, the prosthesis 23 is of the same material as the sleeve 19 or of a material having similar properties. Therefore, movement between the two bodies does not create wear, cause debris or release metal ions which are extremely disadvantageous to the surrounding tissue, inhibits proper healing and the long term durability of the device in the body. The association of the sleeve 19 and the prosthesis 23 provides a self-locking taper connection which allows the implanting surgeon to repeatedly fit the prosthesis 23 with the ball member 25 by way of the sleeve 19, irrespective of the particular surgical situation encountered.

A method for providing attachment of the interchangeable prosthesis 23 using a dissimilar material for the ball member 25 comprises a first step of selecting a properly sized ball member 25 for providing the contact surface 27 which will not induce tissue growth thereto. The ball member 25 must be sized so as to be received within the socket 31 and articulate relative to the socket 31. This assumes, of course, that the socket 31 has already been affixed and attached to the pelvis 33 using a surgical cement or tissue ingrowth commonly known in the art of prosthesis implantation.

The ball member 25 would have the sleeve 19 of a dissimilar material already affixed within the ball member 25. The sleeve 19 may be entirely recessed within the ball member 25 or may extend above and beyond the exterior surface 27 of the ball member 25. Depending upon the particular joint to be replaced, it may be preferable to have the sleeve 19 fully recessed within the ball member 25.

The interior wall 43 of the recess 37 is sized to receive the sleeve 19 and securely hold the sleeve 19 by way of bonding techniques commonly known in the art. The sleeve 19 cannot move relative to the ball member 25. The implanting surgeon selects a prosthesis 23 which would appear to meet the requirements of the particular application depending upon where the top of the femur or other bone to be joined has been resected. The implanting surgeon then joins the selected prosthesis 23 relative to the ball member 25 and implants, a distal end 49 of the prostheses 23 within an intramedullary canal 47 of the femur 11.

Since the proximal stem 21 of the prosthesis 2 has outwardly tapered walls 45, a self-locking taper fit with the inwardly tapered walls 48 of the sleeve 19 provides a secure engagement which can be dissociated if the implanting surgeon decides that the selected prosthesis 23 or the selected ball member 25 is inappropriate for the situation encountered.

As shown in FIG. 2 and FIG. 4, an alternative embodiment of the invention for a similar orthopedic junction 60 releasably connects prosthetic material having different degrees of hardness. Again, a spacer sleeve 51 similarly described heretofore as the sleeve 19 can be recessed within a third recess 53 of a spacer 55 having a distal and conical end 57 sized to be received within the intramedullary canal 47 of the femur 11. The spacer 55 is of a material such as cobalt-chrome-molybdenum alloy to prevent the growth of tissue and bone from the intramedullary canal 47 onto the prosthesis 23. Using such a spacer 55 allows the proper fitting of the prosthesis 21 within the intramedullary canal 47.

The distal end 49 of the prosthesis 23 has an outwardly tapered surface 59 of a size and shape so as to complement an interior surface 61 within a recess 63 (shown in phantom line in FIG. 4) of the spacer sleeve 51. The combination of the distal end 49 of the prosthesis 23 and the recess 63 of the spacer sleeve 51 provides a self-locking taper connection which can securely hold the spacer 55 to the prosthesis 23, yet also dissociate if the surgeon requires a spacer 55 of a different diameter for proper fitting within the intramedullary canal 47.

It should be noted that the embodiment shown in FIG. 3 and the embodiment as shown in FIG. 4 can be combined in a femur-hip joint replacement as collectively shown in FIG. 2. Therefore, the combination provides for a titanium alloy prosthesis 23 which is readily enagageable with a ball member 25 of a dissimilar material such as a cobalt-chrome-molybdenum alloy, as well as a cobalt-chrome-molybdenum spacer 55 insertable within the intramedullary canal 47 of the femur 11.

Such a combination makes for a flexible and interchangeable prosthesis arrangement to allow the implanting surgeon a maximum degree of flexibility in sizing various prosthesis once an implantation operation is underway.

Of course, the inventive method heretofore described may include the further step of selecting the spacer 55 of a size most suitable for providing a contact surface which will not induce tissue growth thereto. The spacer 55 will include the spacer sleeve 51 of a selected material such as titanium alloy. Then, the spacer 53 as well as the spacer sleeve 51 would be implanted in the body and mated with the distal end 49 of the prosthesis 23 to provide secure engagement between the spacer 55 and the distal end 49 of the prosthesis 23.

It should be noted that the spacer sleeve 51 can be entirely recessed within the recess 53 of the spacer 55 or partially extend above the spacer 55. Also, the spacer sleeve 51 may have a closed end 65 which is insertable into the recess 53 of the spacer 55.

It should be appreciated from the foregoing description that the present invention provides a unique apparatus and method for combining materials of different properties, particularly hardness in such combinations which have heretofore proven difficult and yielded adverse results. The invention provides a simple, yet effective way to join prosthetic materials of different types which allows for the overall optimization of the prosthesis in view of the stresses, forces and surrounding environment to either encourage tissue ongrowth or discourage tissue ongrowth at various locations of the overall prosthesis.

The invention is easily manufactured and provides a great degree of flexibility for the implanting surgeon in selecting large numbers and types of prosthesis components for any situation encountered during the implantation operation.

Although the present invention has been described in detail with reference only to the presently-preferred embodiments, it should be appreciated by those ordinarily skilled in the art that various modifications can be made without departing from the invention. Accordingly, the invention is limited only by the following claims.

We claim:

1. An improved orthopedic connector for joining one prosthesis component of a first selected material to another prosthesis component of a second selected material, said second material being dissimilar in hardness to said first material, comprising:
   (a) sleeve means for mating with a mating end of said prosthesis component of said first selected material, said sleeve means having a smooth, nonfrustoconical outer surface and a frustoconical inner surface, said sleeve means being of a material of similar hardness to said first selected material; and
   (b) retaining means for totally constraining said sleeve means within a cavity formed in said prothesis component of said second selected material, said outer surface of said sleeve being in substantially continuous securement interface with a respective interior surface of said cavity, thereby preventing said sleeve means from dissociating from said prosthetic component of said second selected material.

2. An improved orthopedic connector for joining a prosthesis of a selected material as claimed in claim 1, wherein said sleeve means includes an inner recess which is inwardly tapered at a connection end for receiving said mating end of the prosthesis which is tapered outwardly, whereby mating said sleeve means with said mating end of the prosthesis forms a Morse taper connection.

3. An improved orthopedic connector for joining a prosthesis of a selected material as claimed in claim 2, wherein said sleeve means includes a closed end opposite said connection end.

4. An improved orthopedic connector for joining a prosthesis of a selected material as claimed in claim 3, wherein said sleeve means is recessed within said retaining means.

5. An improved orthopedic connector for joining a prosthesis of a selected material as claimed in claim 4, wherein the selected material of the prosthesis is a titanium alloy and the said similar material is a titanium alloy, and wherein said dissimilar material of said retaining means is a cobalt-chrome-molybdenum alloy.

6. A method for providing attachment of an interchangeable prosthesis using dissimilar materials comprising the steps of:
   (a) selecting an implantable retaining means for providing a contact surface which will not induce tissue growth thereto, said retaining means including a sleeve means of a selected material, said sleeve means having a smooth, nonfrustoconical outer surface, said sleeve means being joined to said retaining means by a substantially continuous securement interface therebetween, whereby said sleeve means is totally constrained with respect to said retaining means;
   (b) selecting a prosthesis of said selected material having an end to mate and securably engage said sleeve means, said sleeve means and said prosthesis fixedly securable and separable in the event an alternatively-sized prosthesis must be implanted; and
   (c) implanting said prosthesis and said retaining means in a body and mating said end of said prosthesis with said sleeve means to provide secure engagement between said retaining means and said prosthesis.

7. A method for providing attachment of an interchangeable prosthesis as claimed in claim 6, wherein said sleeve means includes an inner surface which is inwardly-tapered at a connection end for receiving said end of said prosthesis which is tapered outwardly, whereby mating said sleeve means with said end of said prosthesis forms a self-locking taper connection.

8. A method for providing attachment of an interchangeable prosthesis as claimed in claim 7, wherein said sleeve means includes a closed end opposite said connection end.

9. A method for providing attachment of an interchangeable prosthesis as claimed in claim 8, wherein said sleeve means is recessed within said retaining means.

10. A method for providing attachment of an interchangeable prosthesis as claimed in claim 9, wherein said selected material of said sleeve means and said prosthesis is a titanium alloy, and wherein said retaining means is a cobalt-chrome-molybdenum alloy.

11. A method for providing attachment of an interchangeable prosthesis as claimed in claim 10, wherein said prosthesis is of a femoral-type having a intramedullary end which is implantable within an intramedullary canal of a femur, and wherein said retaining means has a convexly rounded exterior surface to slideably engage a socket including a complementing contact surface, said socket being affixed to a pelvis of the body to simulate a hip joint.

12. A method for providing attachment of an interchangeable prosthesis as claimed in claim 6, wherein said end of said prosthesis is of a type which is insertable within an intramedullary canal of the body, and wherein said retaining means has a frustoconical exterior surface having cylindrical walls which engage interior walls of said intramedullary canal, whereby said retaining means acts as a spacer between said sleeve means and said walls of said intramedullary canal and precludes tissue and bone attachment thereto.

13. A method for providing attachment of an interchangeable prosthesis as claimed in claim 6, wherein said prosthesis is of a femoral-type having an intramedullary end which is implantable within an intramedullary canal of a femur, and wherein said retaining means has a convexly rounded exterior surface to slideably engage a socket including a complementing contact surface, said socket being affixed to a pelvis of the body to simulate a hip joint.

14. A method for providing attachment of an interchangeable prosthesis as claimed in claim 13, comprising the further steps of:
   (a) selecting an implantable second retaining means for providing a contact surface which will not induce tissue growth thereto, said second retaining means including a second sleeve means of a selected material and wherein said second sleeve means and said intermedullary end of said prosthesis are fixedly engageable and separable in the event an alternatively-sized prosthesis must be implanted; and
   (b) implanting said second retaining means in the body and mating said intramedullary end of said prosthesis with said second sleeve means to provide secure engagement between said second retaining means and said intramedullary end of said prosthesis.

15. A method for providing attachment of an interchangeable prosthesis as claimed in claim 14, wherein said first sleeve means includes a first inner surface which is inwardly tapered at a first connection end for receiving said end of said prosthesis which is tapered outwardly, whereby mating said first sleeve means with said end of said prosthesis forms a self-locking taper connection, and wherein said second sleeve means includes a second inner surface which is inwardly tapered at a second connection end for receiving said intermedullary end of said prosthesis which is tapered outwardly, whereby mating said second sleeve means with said intramedullary end of said prosthesis forms a second self-locking taper connection.

16. A method for providing attachment of an interchangeable prosthesis as claimed in claim 15, wherein said sleeve means includes a closed end opposite said connection end, and wherein said second sleeve means includes a second closed end opposite said second connection end.

17. A method for providing attachment of an interchangeable prosthesis as claimed in claim 16, wherein said sleeve means is recessed with said retaining means, and wherein said second sleeve means is recessed within said second retaining means, and wherein said retaining mean and second retaining means is a cobalt-chrome-molybdenum alloy and said sleeve means, said second sleeve means and the prosthesis is a titanium alloy.

18. An orthopedic junction for releasably connecting prosthesis materials having differing degrees of hardness comprising:
   (a) an inner component of a first material having a first degree of hardness, said inner component having a smooth, nonfrustoconical outer surface and including a female receptor means having an inner surface for receiving a male end of a prosthesis formed of said first material and having a similar degree of hardness to said inner component, said female receptor means and said male end being complementarily tapered to provide a self-locking taper connector therebetween when said male end is inserted into said female receptor means; and
   (b) an outer component of a second material having a different degree of hardness from said first material, said outer component having a cavity formed therein for partially surrounding said inner component and forming a substantially continuous securement interface with a substantial portion of said outer surface of said inner component, whereby said inner component is totally constrained with respect to said outer component to define a secure and dissociable junction between said outer component and said male end of said prosthesis.

19. An orthopedic junction for releasably connecting prosthetic materials having differing degrees of hardness as claimed in claim 18, wherein said first material is a titanium alloy and wherein said second material is a cobalt-chrome-molybdenum alloy.

20. An orthopedic junction for releasably connecting prosthetic materials having differing degrees of hardness as claimed in claim 19, wherein said outer component has a convexly curved exterior surface of a shape and size to interface with a hip joint socket of a pelvis and said prosthesis is a type which is partially insertable within an intramedullary canal of a femur, thereby providing a hip joint prosthesis of dissimilar metals optimized for greatest durability and implantability.

* * * * *